US011135315B2

(12) United States Patent
Bowler et al.

(10) Patent No.: US 11,135,315 B2
(45) Date of Patent: Oct. 5, 2021

(54) COMPOSITION FOR DETECTING BIOFILMS ON VIABLE TISSUES

(71) Applicant: CONVATEC TECHNOLOGIES INC., Las Vegas, NV (US)

(72) Inventors: Phillip Godfrey Bowler, Flintshire (GB); Daniel Gary Metcalf, Flintshire (GB); David Parsons, Flintshire (GB); Emily Sonia Johnson, Flintshire (GB)

(73) Assignee: CONVATEC TECHNOLOGIES INC., Las Vegas, NV (US)

(*) Notice: Subject to any disclaimer, the term of this patent is extended or adjusted under 35 U.S.C. 154(b) by 0 days.

(21) Appl. No.: 16/295,774

(22) Filed: Mar. 7, 2019

(65) Prior Publication Data
US 2019/0216953 A1 Jul. 18, 2019

Related U.S. Application Data

(63) Continuation of application No. 13/990,755, filed as application No. PCT/GB2011/001665 on Nov. 30, 2011, now abandoned.

(30) Foreign Application Priority Data

Nov. 30, 2010 (GB) ..................... 1020236

(51) Int. Cl.
A61K 49/00 (2006.01)
G01N 33/569 (2006.01)
C12Q 1/04 (2006.01)
G01N 33/533 (2006.01)
G01N 33/58 (2006.01)

(52) U.S. Cl.
CPC ............ A61K 49/0041 (2013.01); C12Q 1/04 (2013.01); G01N 33/533 (2013.01); G01N 33/569 (2013.01); G01N 33/582 (2013.01)

(58) Field of Classification Search
None
See application file for complete search history.

(56) References Cited

U.S. PATENT DOCUMENTS

| 2,396,514 | A | 3/1946 | Kreidl et al. |
| 2,785,106 | A | 3/1957 | Mendelsohn |
| 3,061,469 | A | 10/1962 | Manowitz et al. |
| 3,092,552 | A | 6/1963 | Romans |
| 4,258,056 | A | 3/1981 | Lentsch |
| 4,612,337 | A | 9/1986 | Fox, Jr. et al. |
| 4,655,758 | A | 4/1987 | Ring et al. |
| 4,728,323 | A | 3/1988 | Matson |
| 4,829,129 | A | 5/1989 | Kelley |
| 4,889,654 | A | 12/1989 | Mason et al. |
| 4,906,100 | A | 3/1990 | Rice et al. |
| 4,973,848 | A | 11/1990 | Kolobanov et al. |
| 5,064,652 | A | 11/1991 | Bay |
| 5,326,567 | A | 7/1994 | Capelli |
| 5,340,924 | A | 8/1994 | Tomita et al. |
| 5,407,656 | A | 4/1995 | Roozdar |
| 5,527,534 | A | 6/1996 | Myhling |
| 5,567,495 | A | 10/1996 | Modak et al. |
| 5,616,347 | A | 4/1997 | Alliger et al. |
| 5,662,913 | A | 9/1997 | Capelli |
| 5,670,169 | A * | 9/1997 | Cornell ................ A61K 9/0014 424/488 |
| 5,709,870 | A | 1/1998 | Yoshimura et al. |
| 5,731,083 | A | 3/1998 | Bahia et al. |
| 5,744,151 | A | 4/1998 | Capelli |
| 5,744,155 | A | 4/1998 | Friedman et al. |
| 5,762,620 | A | 6/1998 | Cartmell et al. |
| 5,820,918 | A | 10/1998 | Ronan et al. |
| 5,848,995 | A | 12/1998 | Walder |
| 5,860,947 | A | 1/1999 | Stamler |
| 5,998,488 | A | 12/1999 | Shinohara et al. |
| 6,075,177 | A | 6/2000 | Bahia et al. |
| 6,207,601 | B1 | 3/2001 | Maurer et al. |
| 6,290,496 | B1 | 9/2001 | Azar et al. |
| 6,413,556 | B1 | 7/2002 | Bathurst et al. |
| 6,468,965 | B1 | 10/2002 | Cutler |
| 6,548,730 | B1 | 4/2003 | Patel et al. |
| 6,555,508 | B1 | 4/2003 | Paul et al. |
| 6,605,751 | B1 | 8/2003 | Gibbins et al. |
| 6,669,981 | B2 | 12/2003 | Parsons et al. |
| 6,750,262 | B1 | 6/2004 | Haehnle et al. |
| 6,753,063 | B1 | 6/2004 | Pung et al. |
| 7,033,511 | B2 | 4/2006 | Zawada et al. |
| 7,267,828 | B2 | 9/2007 | Parsons et al. |
| 8,637,072 | B2 | 1/2014 | Kershaw et al. |

(Continued)

FOREIGN PATENT DOCUMENTS

CA 2745059 A1 6/2010
CN 101076251 A 11/2007

(Continued)

OTHER PUBLICATIONS

510(k) Premarket Notification, AQUACEL and AQUACEL Ag, Section 5: 510(k) Summary revised Apr. 21, 2008, 6 pages.
AMR: a major European and Global challenge: fact sheet. Antimicrobial Resistance—European Commission (EC—AMR) Sep. 8, 2017. https://ec.europa.eu/health/amr/sites/amr/files/amr_factsheet_en.pdf. Accessed Jul. 2, 2018.
Anwar H, Dasgupta M, Costerton J. Testing the susceptibility of bacteria in biofilms to antibacterial agents. Antimicrob Agents Chemother. 1990; 34: 2043-2046.
Arata, J. Staphylococcus aureus and the skin. Japanese Journal of Chemotherapy, 49(3):147-156, 2001.

(Continued)

Primary Examiner — Jennifer Lamberski
(74) Attorney, Agent, or Firm — Taft Stettinius & Hollister LLP; Ryan O. White; Derek B. Lavender

(57) ABSTRACT

A staining composition for use in making biofilm detectable on viable tissue wherein the composition preferentially stains the biofilm and comprises a staining agent in a quantity effective to stain the biofilm and render it detectable.

19 Claims, 5 Drawing Sheets

(56) References Cited

U.S. PATENT DOCUMENTS

| | | |
|---|---|---|
| 9,149,035 B2 | 10/2015 | Percival et al. |
| 9,545,390 B2 | 1/2017 | Percival et al. |
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |

(56) References Cited

U.S. PATENT DOCUMENTS

| | | |
|---|---|---|
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2002/0091074 A1 | 7/2002 | Wooley et al. |
| 2002/0160941 A1 | 10/2002 | Kruzel |
| 2002/0172709 A1 | 11/2002 | Nielsen et al. |
| 2002/0183808 A1 | 12/2002 | Biel |
| 2003/0180345 A1 | 9/2003 | Hill et al. |
| 2003/0180346 A1 | 9/2003 | Woods |
| 2004/0001880 A1 | 1/2004 | Bowler et al. |
| 2004/0247652 A1 | 12/2004 | Sabesan |
| 2005/0059731 A1 | 3/2005 | Albrecht et al. |
| 2006/0019571 A1 | 1/2006 | Lange et al. |
| 2006/0051385 A1 | 3/2006 | Scholz |
| 2006/0051430 A1 | 3/2006 | Arata et al. |
| 2006/0115440 A1 | 6/2006 | Arata et al. |
| 2006/0155260 A1 | 7/2006 | Blott et al. |
| 2006/0172000 A1 | 8/2006 | Cullen et al. |
| 2006/0234959 A1 | 10/2006 | Biel et al. |
| 2006/0254988 A1 | 11/2006 | Frampton |
| 2007/0042024 A1 | 2/2007 | Gladman et al. |
| 2007/0134136 A1 | 6/2007 | Polyakov et al. |
| 2007/0166399 A1 | 7/2007 | Burton et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2007/0255192 A1 | 11/2007 | Patel et al. |
| 2008/0112920 A1 | 5/2008 | Chia et al. |
| 2008/0188558 A1 | 8/2008 | Godal et al. |
| 2008/0226724 A1 | 9/2008 | Ji et al. |
| 2009/0012440 A1 | 1/2009 | Bray et al. |
| 2009/0177135 A1 | 7/2009 | Rogers et al. |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0113537 A1 | 5/2010 | Nonaka |
| 2010/0125233 A1 | 5/2010 | Edward S. et al. |
| 2010/0125258 A1 | 5/2010 | Coulthard et al. |
| 2010/0129633 A1 | 5/2010 | Law |
| 2010/0137775 A1 | 6/2010 | Hu et al. |
| 2010/0185163 A1 | 7/2010 | Heagle |
| 2010/0298790 A1 | 11/2010 | Guidi et al. |
| 2010/0310845 A1 | 12/2010 | Bond et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0117025 A1 | 5/2011 | Dacosta et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0237994 A1 | 9/2011 | Russ et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0319808 A1 | 12/2011 | Bowler et al. |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0202398 A1 | 8/2012 | Marshall et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0161728 A1 | 6/2014 | Bowler et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0101207 A1 | 4/2016 | Parsons et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0079276 A1 | 3/2017 | Percival et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0347661 A1 | 12/2017 | Parsons |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |

(56) References Cited

U.S. PATENT DOCUMENTS

| | | |
|---|---|---|
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0216953 A1 | 7/2019 | Bowler et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |

(56) References Cited

U.S. PATENT DOCUMENTS

| | | |
|---|---|---|
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| CN | 101331263 A | 12/2008 |
| CN | 105407930 A | 3/2016 |

(56) References Cited

FOREIGN PATENT DOCUMENTS

| | | | |
|---|---|---|---|
| EP | 0616650 A1 | 9/1994 |
| EP | 0680344 A1 | 11/1995 |
| EP | 1158859 A1 | 12/2001 |
| EP | 1318842 A1 | 6/2003 |
| EP | 1343510 A1 | 9/2003 |
| EP | 1425050 A1 | 6/2004 |
| EP | 1557088 A1 | 7/2005 |
| EP | 1882482 A2 | 1/2008 |
| EP | 1925719 A1 | 5/2008 |
| EP | 1343510 B1 | 5/2010 |
| EP | 2262545 A2 | 12/2010 |
| EP | 2996730 A1 | 3/2016 |
| EP | 3187204 A1 | 7/2017 |
| EP | 3241439 A1 | 11/2017 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| FR | 2604900 A1 | 4/1988 |
| GB | 735462 A | 8/1955 |
| GB | 1105829 A | 3/1968 |
| GB | 2094802 A | 9/1982 |
| GB | 2220881 A | 1/1990 |
| GB | 2579211 A | 6/2020 |
| GB | 2579368 A | 6/2020 |
| JP | S5138427 A | 3/1976 |
| JP | H04282311 A | 10/1992 |
| JP | H0782121 A | 3/1995 |
| JP | H07502081 A | 3/1995 |
| JP | H08505790 A | 6/1996 |
| JP | 2000510539 A | 8/2000 |
| JP | 2003052725 A | 2/2003 |
| JP | 2003510475 A | 3/2003 |
| JP | 2003512095 A | 4/2003 |
| JP | 2003531828 A | 10/2003 |
| JP | 2005210997 A | 8/2005 |
| JP | 2007501683 A | 2/2007 |
| JP | 2007509034 A | 4/2007 |
| JP | 2007167266 A | 7/2007 |
| JP | 2007167266 A | 7/2007 |
| JP | 2007532606 A | 11/2007 |
| JP | 2008502735 A | 1/2008 |
| JP | 2008038293 A | 2/2008 |
| JP | 2008503557 A | 2/2008 |
| JP | 2008507327 A | 3/2008 |
| JP | 2008526997 A | 7/2008 |
| JP | 2009519312 A | 5/2009 |
| JP | 2010508346 A | 3/2010 |
| JP | 2010155963 A | 7/2010 |
| JP | 2012512857 A | 6/2012 |
| JP | 2016040294 A | 3/2016 |
| JP | 2016519966 A | 7/2016 |
| KR | 100868574 B1 | 11/2008 |
| RU | 2092180 C1 | 10/1997 |
| WO | WO-8401721 A1 | 5/1984 |
| WO | WO-9218098 A1 | 10/1992 |
| WO | WO-9312275 A1 | 6/1993 |
| WO | WO-9319152 A1 | 9/1993 |
| WO | WO-9402022 A1 | 2/1994 |
| WO | WO-9416746 A1 | 8/1994 |
| WO | WO-9601119 A1 | 1/1996 |
| WO | WO-9702313 A1 | 1/1997 |
| WO | WO-9806260 A1 | 2/1998 |
| WO | WO-9846818 A1 | 10/1998 |
| WO | WO-0054593 A1 | 9/2000 |
| WO | WO-0072874 A1 | 12/2000 |
| WO | WO-0123653 A1 | 4/2001 |
| WO | WO-0124839 A1 | 4/2001 |
| WO | WO-0128338 A2 | 4/2001 |
| WO | WO-0128600 A1 | 4/2001 |
| WO | WO-0137936 A1 | 5/2001 |
| WO | WO-0162289 A2 | 8/2001 |
| WO | WO-0243743 A1 | 6/2002 |
| WO | WO-02055060 A2 | 7/2002 |
| WO | WO-02078755 A2 | 10/2002 |
| WO | WO-03022317 A1 | 3/2003 |
| WO | WO-03047341 A2 | 6/2003 |
| WO | WO-03068247 A1 | 8/2003 |
| WO | WO-2004028461 A2 | 4/2004 |
| WO | WO-2004035718 A2 | 4/2004 |
| WO | WO-2004056346 A1 | 7/2004 |
| WO | 2004105809 A1 | 12/2004 |
| WO | WO-2004108093 A2 | 12/2004 |
| WO | 2005018543 A2 | 3/2005 |
| WO | WO-2005020915 A2 | 3/2005 |
| WO | WO-2005032459 A2 | 4/2005 |
| WO | WO-2005079582 A1 | 9/2005 |
| WO | WO-2005099757 A1 | 10/2005 |
| WO | WO-2005123103 A2 | 12/2005 |
| WO | WO-2006000765 A1 | 1/2006 |
| WO | WO-2006015317 A2 | 2/2006 |
| WO | WO-2006022970 A1 | 3/2006 |
| WO | WO-2006029213 A1 | 3/2006 |
| WO | WO-2006111624 A2 | 10/2006 |
| WO | WO-2007005720 A2 | 1/2007 |
| WO | WO-2007068938 A2 | 6/2007 |
| WO | WO-2008035734 A1 | 3/2008 |
| WO | WO-2009130608 A2 | 10/2009 |
| WO | WO-2010070292 A1 | 6/2010 |
| WO | 2011121394 A1 | 10/2011 |
| WO | 2011135284 A1 | 11/2011 |
| WO | 2011144888 A1 | 11/2011 |
| WO | WO-2012061225 A2 | 5/2012 |
| WO | WO-2012072980 A1 | 6/2012 |
| WO | WO-2012136968 A1 | 10/2012 |
| WO | 2013015827 A2 | 1/2013 |
| WO | 2013126049 A1 | 8/2013 |
| WO | 2014014842 A1 | 1/2014 |
| WO | WO-2014186590 A1 | 11/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |

(56) References Cited

FOREIGN PATENT DOCUMENTS

| | | |
|---|---|---|
| WO | 2019219613 A1 | 11/2019 |
| WO | 2019234365 A1 | 12/2019 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020605062 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020159548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |

OTHER PUBLICATIONS

Australia Patent Application No. 2014265336 Examiner's First Report dated Mar. 29, 2017.
Australian Patent Application No. 2013366038 Examination Report No. 2 dated Jun. 19, 2018.
Australian Patent Application No. 2017201084 Examination Report No. 1 dated May 18, 2018.
Australian Patent Application No. 2014265336 Second Examination Report dated Mar. 26, 2018.
Banin et al., Chelator-induced dispersal and killing of Pseudomonas aeruginosa cells in a biofilm. Applied and Environmental Microbiology, 72(3):2064-2069, 2006.
Bay L, Kragh K, Eickhardt S, et al. Bacterial aggregates establish at the edges of acute epidermal wounds. Adv Wound Care. 2018; 7: 105-13.
Bohn G, Liden B, Schultz G, et al. Ovine-based collagen matrix dressing: Next-generation collagen dressing for wound care. Adv Wound Care. 2016; 5: 1-10.
Bowler et al., Dressing conformability and silver-containing wound dressings. Wounds U.K., 6:14-20 (2010).
Bowler P. Antibiotic resistance and biofilm tolerance: a combined threat in the treatment of chronic infections. J Wound Care. 2018 27: 273-277.
Bowler P, Jones S, Davies B, Coyle E. Infection control properties of some wound dressings. J Wound Care. 1999; 8: 499-502.
Bowler P, Jones S, Towers V, et al. Dressing conformability and silver-containing wound dressings. Wounds UK. 2010; 6: 14-20.
Bowler P, Parsons D. Combatting wound biofilm and recalcitrance with a novel anti-biofilm Hydrofiber® wound dressing. Wound Medicine. 2016; 14: 6-11.
Bryant R, Nix D. Principles for practice development to facilitate outcomes and productivity. In Bryant R and Nix D, eds. Acute and Chronic Wounds: Current Management Concepts. 5th ed. St. Louis, MO: Elsevier; 2016: 1-20.
Canadian Patent Application No. 2834871 Office Action dated Oct. 1, 2018.
Canadian Patent Application No. 2,745,059 Office Action dated Apr. 20, 2018.
Canadian Patent Application No. 2,745,059 Office Action dated Aug. 2, 2017.
Canadian Patent Application No. 2,745,059 Office Action dated Dec. 17, 2018.
Canadian Patent Application No. 2,745,059 Office Action dated Oct. 25, 2016.
Canadian Patent Application No. 2,819,303 Office Action dated Oct. 24, 2017.
Canadian Patent Application No. 2,834,871 Office Action dated Jan. 31, 2018.
Capinera et al., Insectional activity of photoactive dyes to American and migratory grasshoppers (*Orthoptera acrididae*). J.Econ. Entomol., 92(3):662-666, 2000.
Cavaliere R, Ball J, Turnbull L, Whitchurch C. The biofilm matrix destabilizers, EDTA and DNaseI, enhance the susceptibility of nontypeable Hemophilus influenzae biofilms to treatment with ampicillin and ciprofloxacin. Microbiology. 2014; 3: 557-67.
Centers for Disease Control and Prevention. Antibiotic Resistance Threats in the United States. 2013. http://www.cdc.gov/ drugresistance/ threat-report-2013/pdf/ar-threats-2013-508.pdf. Accessed Aug. 1, 2018.
Ceri et al., The Calgary biofilm device: New technology for rapid determination of antibiotic susceptibilities of bacterial biofilms. Journal of Clinical Microbiology, 37(6):1771-1776, 1999.
Chan B, Cadarette S, Wodchis W, Wong J, Mittmann N, Kran M. Cost-of-illness studies in chronic ulcers: A systemic review. J Wound Care. 2017; 26: S4-S15.
Chemburu et al., Light-induced biocidal action of conjugated polyelectrolytes supported on colloids Langmuir, 24:11053-11062 (2008).
Chile Patent Application No. 3274-2015 Office Action dated Jun. 20, 2017.
Chile Patent Application No. 3274-2015 second Office Action dated Jan. 22, 2018.
Chinese Patent Application No. 201180066375.2 Reexamination Notice dated Jul. 3, 2017.
Chinese Patent Application No. 201180066375.2 Office Action dated Sep. 26, 2016.
Chinese Patent Application No. 201180066375.2 Reexamination Decision dated Dec. 20, 2017.
Chinese Patent Application No. 201280027537.6 Chinese Third Office Action dated Mar. 2, 2016.
Chinese Patent Application No. 201280027537,6 Decision of Reexamination dated Oct. 27, 2017.
Chinese Patent Application No. 201280027537.6 Office Action dated Sep. 12, 2016.
Chinese Patent Application No. 201280027537.6 Reexamination Notice dated Jun. 8, 2017.
Chinese Patent Application No. 201380073403.2 Third Office Action dated Mar. 26, 2018.
Chinese Patent Application No. 201480028155.4 Decision on Rejection dated Nov. 21, 2018.
Chinese Patent Application No. 201480028155.4 First Office Action dated Apr. 18, 2017.
Chinese Patent Application No. 201480028155.4 Office Action dated Mar. 22, 2018.
Ciofu O, Rojo-Molinero E, Macia M, Oliver A. Antibiotic treatment of biofilm infections. APMIS. 2017; 125: 304-19.

(56) References Cited

OTHER PUBLICATIONS

Costerton J, Geesey G, Cheng K. How bacteria stick. Sci Am. 1978; 238: 86-95.
Costerton J, Irvin R, Cheng K. The bacterial glycocalyx in nature and disease. Ann Rev Microbiol. 1981; 35: 299-324.
Costerton J, Stewart P, Greenberg E. Bacterial biofilms: a common cause of persistent infections. Science. 1999; 284: 1318-22.
Costerton JW. Bacterial biofilms in nature and disease. Ann Rev Microbiol. 1987; 41: 435-64.
Database Biosis, Biosciences Information Service, Philadelphia, PA, 1992, Kida N., et al., "Effect of PH on Preferential Antibacterial Activity of Ethylenediaminetetraacetic Acid EDTA", XP002485724, Database Accession No. PREV199294118093.
Database Biosis, Biosciences Information Service, Philadelphia, PA, 2005, Percival, L, etal., "Tetrasodium EDTA as a novel central venous catheter lock solution against biofilm", XP002485725, Database Accession No. PREV200600021247.
Database CA, Chemical Abstracts Service, Columbus, Ohio, US; Izzat, I.N., et al., "Effect of varying concentrations o EDTA on the antimicrobial properties of cutting fluid preservatives", 1979, XP002485722, STN-International Database Accession No. 93:62380.
Database CA, Chemical Abstracts Service, Columbus, Ohio, US; Reybrouck, G., et al., "Effect of ethylenediaminetetraacetate on the germicidal action of disinfectants against Pseudomonas aeruginosa", XP002485721, STN-International Database Accession No. 72:11588, 1969.
Database Medline, US National Library of Medicine, Bethesda, MD, 1988, Kaur, P., et al., "Effect of certain chelating agents on the antibacterial action of silver nitrate", XP002485723, Database Accession No. NLM3143759.
Demidova and Hamblin, Photodynamic therapy targeted to pathogens Int. J. Immunopathol Pharmacol., 17(3):245-254, 2004.
Dini V, Salvo P, Janowska A, Di Francesco F, Barbini A, Romanelli M. Correlation between wound temperature obtained with an infrared camera and clinical wound bed score in venous leg ulcers. Wounds. 2015; 27: 274-8.
Dougherty et al., Photodynamic therapy. Journal of the National Cancer Institute, 90(12): 889-905, 1998.
Doughty D, Sparks B. Wound healing physiology and factors that affect the wound repair process. In Bryant R and Nix D, eds. Acute and Chronic Wounds: Current Management Concepts. 5th ed. St. Louis, MO: Elsevier; 2016: 63-81.
Eming S, Martin P, Tomic-Canic M. Wound repair and regeneration: mechanisms, signaling, and translation. Sci Transl Med. 2014; 6: 57-72. doi: 10.1126/scitranslmed.3009337.
Etebu E, Arikekpar I. Antibiotics: Classification and mechanisms of action with emphasis on molecular perspective. Int J of Appl Microbiol and Biothech Res. 2016; 4: 90-101. http://www.bluepenjournals.org/ijambr/pdf/2016/October/Etebu_and_Arikekpar.pdf. Accessed Aug. 8, 2018.
European Centre for Disease Prevention and Control (ECDC). Proposals for EU Guidelines on the Prudent Use of Antimicrobials in Humans. Stockholm: ECDC; 2017. http://ecdc.europa.eu/en/publications/_layouts/forms/Publication_DispForm.aspx?List=4f55ad51-4aed-4d32-b960-af70113dbb90&ID=1643. Accessed Jul. 2, 2018.
European Patent Application No. 09795521.5 Communication dated Mar. 24, 2017.
European Patent Application No. 09795521.5 Office Action dated May 9, 2018.
European Patent Application No. 12719420.7 Communication dated Jul. 20, 2016.
European Patent Application No. 12719420.7 Examination Report dated Apr. 5, 2017.
European Patent Application No. 12719420.7 Examination Report dated Aug. 7, 2018.
European Patent Application No. 13821122.2 Communication dated Oct. 30, 2017.
European Patent Application No. 14797983.5 Supplementary European Search Report dated Dec. 6, 2016.
European Patent Application No. 17163418.1 extended European Search Report dated Sep. 17, 2017.
European Patent Application No. EP 06820530.1 Communication dated Apr. 7, 2016.
European Patent Application No. EP 06820530.1 Communication dated Jan. 30, 2013.
European Patent Application No. EP 06820530.1 Communication dated Mar. 30, 2009.
FDA website on Medical Devices, Premarket Notification (510k), 4 pages, 2013.
Fife C, Carter M, Walker D, Thomson B. Wound care outcomes and associated cost among patients treated in US outpatient wound centers: Data from the US Wound Registry. Wounds. 2012; 24: 10-7.
Finnegan S, Percival S. EDTA: an antimicrobial and antibiofilm agent for use in wound care. Adv Wound Care. 2015; 4: 415-21.
Fleming D, Rumbaugh K. Approaches to dispersing medical biofilms. Microorganisms. 2017; 5: 1-16.
Frykberg R, Banks J. Challenges in the treatment of chronic wounds. Adv Wound Care. 2015; 4: 560-82.
Gardner S, Frantz R, Doebbeling B. The validity of the clinical signs and symptoms used to identify localized chronic wound infection. Wound Repair Regen. 2001; 9: 178-86.
Gardner S, Hillis S, Frantz R. Clinical signs of infection in diabetic foot ulcers with high microbial load. Biol Res Nurs. 2009; 11: 119-28.
Gilbert, et al., The Use of Poloxamer Hydrogels for the Assessment of Biofilm Susceptibility Towards Biocide Treatments, Journal of Applied Microbiology, 85:985-990, 1998.
Gilchrist M, Seaton R. Outpatient parenteral antimicrobial therapy and antimicrobial stewardship: challenges and checklists. J Antimicrob Chemother. 2015; 70: 965-70.
Gottrup F. A specialized wound-healing center concept: importance of a multidisciplinary department structure and surgical treatment facilities in the treatment of chronic wounds. Am J Surg. 2004; 187: S38-S43.
Gottrup F, Apelqvist J, Bjarnsholt T, et al. Antimicrobials and non-healing wounds: Evidence, controversies and suggestions—key messages. J Wound Care. 2014; 23: 477-8, 480, 482.
Guest JF, Vowden K. The health economic burden that acute and chronic wounds impose on an average clinical commissioning group/health board in the UK. J Wound Care. 2017; 26: 292-303.
Harding K, Szczepkowski M, Mikosiński J, et al. Safety and performance evaluation of a next-generation antimicrobial dressing in patients with chronic venous leg ulcers. Int Wound J. 2016; 13: 442-8.
Harrison-Balestra et al., A wound isolated*Pseudomonas aeruginosa*grows a biofilm in vitro within 10 hours and is visualized by light microscopy. Dermatol. Surgery, 29(6):631-635, 2003.
Hobot et al., Effect of Hydrofiber wound dressings on bacterial ultrastructure. J Electron Microsc (Tokyo). 57(2):67-75 (2008).
Howell J, Stair T, Howell A, Mundt D, Falcone A, Peters S. The effect of scrubbing and irrigation with normal saline, povidone iodine, and cefazolin on wound bacterial counts in a Guinea pig model. Am J Emerg Med. 1993; 11: 134-38.
Hurlow J, Blanz E, Gaddy J. Clinical investigation of biofilm in non-healing wounds by high resolution microscopy techniques. J Wound Care. 2016; 25(suppl 9): S11-S22.
Indian Patent Application No. 9392/DELNP/2013 First Examination Report dated Feb. 23, 2018.
Indian Patent Application No. 5856/DELNP/2013 First Examination Report dated Jun. 20, 2018.
International Wound Infection Institute (IWII). Wound infection in clinical practice. Wounds International, 2016. http://www.woundinfection-institute.com/wp-content/uploads/2017/03/IWII-Wound-infection-in-clinical-practice.pdf. Accessed Jul. 2, 2018.
James G, Swogger E, Wolcott R, et al. Biofilms in chronic wounds. Wound Repair Regen. 2008; 16: 37-44.
Japan Patent Application No. 2016-514095 Office Action dated Feb. 20, 2018.
Japanese Patent Application No. 2017-112806 Official Action dated Mar. 6, 2018.
Japanese Patent Application No. 2013-541415 Final Rejection dated Jun. 14, 2016.

(56) References Cited

OTHER PUBLICATIONS

Japanese Patent Application No. 2014-242257 Office Action dated Apr. 5, 2016 (English translation is provided).
Japanese Patent Application No. 2014-242257 Office Action dated May 23, 2017.
Japanese Patent Application No. 2014-543972 Office Action dated Dec. 20, 2016.
Japanese Patent Application No. 2015-200279 Office Action dated Aug. 31, 2017.
Japanese Patent Application No. 2015-200279 Office Action dated Feb. 7, 2017.
Japanese Patent Application No. 2015-200279 Office Action dated Jul. 12, 2016.
Japanese Patent Application No. 2015-548762 Office Action dated Jul. 31, 2018.
Japanese Patent Application No. 2015-548762 Office Action dated Oct. 10, 2017.
Japanese Patent Application No. 2016-154639 Office Action dated Jun. 8, 2017.
Japanese Patent Application No. 2016-202835 Office Action dated Jun. 20, 2017.
Japanese Patent Application No. 2016-202835 Office Action dated Mar. 6, 2018.
Jasovský D, Littmann J, Zorzet A, Cars O. Antimicrobial resistance—a threat to the world's sustainable development. Upsala J Med Sci. 2016; 121: 159-64.
Johani K, Malone M, Jensen S, et al. Microscopy visualisation confirms multi-species biofilms are ubiquitous in diabetic foot ulcers. Int Wound J. 2017; 14: 1160-9.
Jones et al., Antimicrobial activity of silver-containing dressings is influenced by dressing conformability with a wound surface. Wounds, 17:263-270 (2005).
Kapoor et al., Fluorescence and absorption spectra of Rose-Bengal dye in the presence of surfactants. Journal of Luminescence, 22(4):429-439, 1981. (Abstract only).
Kaur and Vadehra, Effect of certain chelating agents on the antibacterial action of silver nitrate. Journal of Hygiene, Epidemiology, Microbiology, and Immunology, 32(3):299-306, 1988. (retrieved from Medline, NLM3143759).
Keast D, Swanson T, Carville K, Fletcher J, Schultz G, Black J. Ten top tips . . . understanding and managing wound biofilm. Wounds International. 2014; 5: 20-3.
Kharkevich, D.A., Pharmacology:Textbook. Geotar-Media, p. 66-71, 2006.
Kim D, Namen W, Moore J, Buchanan M, Hayes V, Myntti, M, Hakaim A. Clinical assessment of a biofilm-disrupting agent for the management of chronic wounds compared with standard of care: a therapeutic approach. Wounds. 2018; 30: 120-30.
Kita et al., pH-Dependent preferential antibacterial activity of Ethylenediaminetetraacetic acid (EDTA). Japanese Journal of Bacteriology, 47(4):6 pages, 1992.
Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.
Kryukov et al., the role of bacteriological examination in diagnosis of chronic tonsillitis. Becthnk 3:35-38, 2008.
Lazarus G, Cooper D, Knighton D, Percoraro R, Rodeheaver G, Robson M. Definitions and guidelines for assessment of wounds and evaluation of healing. Wound Repair Regen. 1994; 2: 165-70.
Lewis K. Persister cells. Ann Rev Microbiol. 2010; 64: 357-72.
Lineaweaver et al., Topical antimicrobial toxicity. Arch Surg., 120(3):267-70 (1985).
Lipsky B, Aragón-Sánchez J, Diggle M, et al. IWGDF guidance on the diagnosis and management of foot infections in persons with diabetes. Diabetes Metab Res Rev. 2016; 32: 45-74.
Lipsky B, Dryden M, Gottrup F, et al. Antimicrobial stewardship in wound care: A position paper from the British society for antimicrobial chemotherapy and European wound management association. J Antimicrob Chemother 2016; 71: 3026-35.
Lipsky B. Medical treatment of diabetic foot infections. Clin Infect Dis. 2004; 39: S104-S114.
Lipsky B, Peters E, Senneville E, et al. Expert opinion on the management of infections in the diabetic foot. Diabetes Metab Res Rev. 2012; 28(suppl 1): 163-78.
Macia M, Roho-Molinero E, Oliver A. Antimicrobial susceptibility testing in biofilm-growing bacteria. Clin Microbiol Infect. 2014; 20: 981-90.
Malone M, Bjarnsholt T, McBain A, et al. The prevalence of biofilms in chronic wounds: a systematic review and meta-analysis of published data. J Wound Care. 2017; 26: 20-5.
McDonnell G, Russell A. Antiseptics and disinfectants: Activity, action, and resistance. Clin Microbiol Rev. 1999; 12: 147-79.
Meredith K, Burke N, Brownley H, et al. Antimicrobial efficacy of enhanced and standard silver wound dressings in an in vitro mature bioburden model. Symposium on Advanced Wound Care. 2018 Poster presentation: Las Vegas.
Metcalf D, Bowler P. Biofilm delays wound healing: A review of the evidence. Burns Trauma. 2013; 1: 5-12.
Metcalf D, Bowler P. Clinical Impact of an enhanced antimicrobial dressing in non-healing wounds previously managed with antibiotics. Symposium on Advanced Wound Care. 2018 Poster presentation: Las Vegas.
Metcalf D, Bowler P, Parsons D. In: Dhanasekaran D, ed. Wound Biofilm and Therapeutic Strategies, Microbial Biofilms—Importance and Applications. Rijeka, Croatia: InTech; 2016. https://www.intechopen.com/books/microbial-biofilms-importance-and-applications/wound-biofilm-and-therapeutic-strategies. Accessed Aug. 8, 2018.
Metcalf D, Parsons D, Bowler P. A next-generation antimicrobial wound dressing: a real-life clinical evaluation in the UK and Ireland. J Wound Care. 2016; 25: 132-8.
Metcalf D, Parsons D, Bowler P. Clinical safety and effectiveness evaluation of a new antimicrobial wound dressing designed to manage exudate, infection and biofilm. Int Wound J. 2017; 14: 203-13.
Mexican Patent Application No. MX/a/2013/006090 Official Action dated Jun. 7, 2016.
Mexican Patent Application No. MX/a/2015/015197 Office Action dated Mar. 2, 2018.
Muller et al. pH-dependent formation of ethylenediaminetetraacetic acid supramolecular aggregates. FEBS Lett 340:17-21 (1994).
Nagai et al., Suppressive effects of EDTA for Pseudomonas aeruginosa products biofiim STN CAPLUS, Jan. 1, 1996, 1 page. XP002122029.
Nagoba B, Suryawanshi N, Wadher B, Selkar S. Acidic environment and wound healing: a review. Wounds. 2015; 27: 5-11.
Newman G, Walker M, Hobot J, Bowler P. Visualisation of bacterial sequestration and bactericidal activity within hydrating Hydrofiber wound dressings. Biomaterials. 2006; 27: 1129-39.
Nickel J, Wright J, Ruseska I, Marrie T, Whitfield C, Costerton J. Antibiotic resistance of pseudomonas aeruginosa colonizing a urinary catheter in vitro. Eur J Clin Microbiol. 1985; 4: 213-18.
Nix D, Pierce B, Haugen V. Eliminating non-compliance. In Bryant R and Nix D, eds. Acute and Chronic Wounds: Current Management Concepts. 5th ed. St. Louis, MO: Elsevier; 2016: 428-40.
Nussbaum S, Carter M, Fife C, et al. An economic evaluation of the impact, cost, and Medicare policy implications of chronic nonhealing wounds. Value Health. 2018; 21: 27-32.
Olsen I. Biofilm-specific antibiotic tolerance and resistance. Eur J Clin Microbiol Infect Dis. 2015; 34: 877-86.
Ono, N. A Semi-quantitative measurement of glycocalyx and an ATP bioluminescent assay for the analysis of Pseudomonas Aeruginosa biofilm. The Japanese Journal of Urology, 86(9):1440-1449, 1995.
Ovington, The Value of Silver in Wound Management. Podiatry Today, Dec. 1999, 12(7):59-62. (marked as Exhibit 3 at the Deposition of Fiona Adam).
Parikh et al., Antimicrobial silver/sodium carboxymethyl cotton dressings for burn wounds Textile Research Journal, 75(2):134-138 (2005).
Parsons et al., Enhanced Performance and Mode of Action of a Novel Antibiofilm Hydrofiber Wound Dressing. BioMed Research International 2016: ID 7616471:1-14 (2016).

(56) References Cited

OTHER PUBLICATIONS

PCT Patent Application No. PCT/GB2012/000329 International Search Report and Written Opinion dated Jul. 17, 2012.
PCT Patent Application No. PCT/US2014/038224 International Preliminary Report on Patentability dated Nov. 17, 2015.
PCT Patent Application No. PCT/US2014/038224 International Search Report dated Sep. 15, 2014.
PCT Patent Application No. PCT/US2014/038224 Written Opinion dated Sep. 15, 2014.
PCT/GB2006/004691 International Preliminary Report on Patentability dated Aug. 12, 2008.
PCT/GB2006/004691 International Search Report dated Jul. 7, 2008.
PCT/GB2006/004691 Written Opinion dated Jul. 7, 2008.
PCT/GB2009/002912 International Preliminary Report on Patentability dated Jun. 21, 2011.
PCT/GB2009/002912 International Search Report and Written Opinion dated Mar. 2, 2010.
PCT/GB2011/001665 International Preliminary Report on Patentability dated Jun. 4, 2013.
PCT/GB2011/001665 International Search Report dated Mar. 2, 2012.
PCT/GB2011/001665 Written Opinion dated Mar. 2, 2012.
Pennington JA. , A review of iodine toxicity reports. J Am Diet Assoc., 90(11):1571-81 (1990).
Percival et al., Tetrasodium EDTA as a novel central venous catheter lock solution against biofilm. Infection Control and Hospital Epidemiology, 26(6):515-519, 2005.
Percival S, Bowler P. Biofilms and their potential role in wound healing. Wounds. 2004; 16: 234-240.
Petchiappan A, Chatterji D. Antibiotic resistance: Current perspectives. ACS Omega 2017, 2, 7400-7409. https://www.researchgate.net/publication/321019969/download. Accessed Jul. 7, 2018.
Phillips T. Chronic cutaneous ulcers: Etiology and epidemiology. J Invest Dermatol. 1994; 102: 38S-41S.
Poon and Burd, In vitro cytotoxity of silver: implication for clinical wound care. Burns. 30(2):140-7 (2004).
Ramage et al., Inhibition on Candida albicans biofilm formation using divalent cation chelators (EDTA), Mycopathologia, 164:301-306, 2007.
Reybrouck et al., Effect of ethylenediamine tetraacetate on the germicidal action of disinfectants against "Pseudomona." Acta Clinica Belgica, 24(1):32-41, 1969.
Rhoads D, Wolcott R, Percival S. Biofilms in wounds: management strategies. J Wound Care. 2008; 17: 502-9.
Rodeheaver G, Ratliff C. Wound cleansing, wound irrigation, wound disinfection. In: Krasner D, van Rijswijk L, eds. Chronic Wound Care: The Essentials e-Book. Malvern, PA: HMP; 2018: 47-62. Available at: https://s3.amazonaws.com/whywoundcare/Files/Chapter+5.pdf. Accessed Jul. 7, 2018.
Romanelli M, Vowden K, Weir D. Exudate management made easy. Wounds International. 2014. http://www.woundsinternational.com/made-easys/view/exudate-management-made-easy-1. Accessed Jul. 11, 2018.
Rondas A, Schols J, Stobberingh E, Price P. Definition of infection in chronic wounds by Dutch nursing home physicians. Int Wound J. 2009; 6: 267-74.
Russian Patent Application No. 2015153446 Office Action and Search Report dated Apr. 23, 2018.
Russian Patent Application No. 2013129866 Office Action dated Oct. 21, 2016.
Russian Patent Application No. 2013129866/10 Protocol of a Meeting with the Examiner dated Jun. 14, 2017.
Russian Patent Application No. 2013149176 Official Action dated Feb. 21, 2018.
Russian Patent Application No. 2013149176 Official Action dated Jun. 2, 2016.
Russian Patent Application No. 2015153446 Office Action dated Feb. 10, 2016 (In Russian).
Said et al., An in vitro test of the efficacy of an anti-biofilm wound dressing.Int J Pharm. 474(1-2):177-181 (2014).
Saudi Arabia Patent Application No. 515370133 2nd Examination Report dated Feb. 6, 2017.
Savage V, Chopra I, ONeill A. *Staphylococcus aureus* biofilms promote horizontal transfer of antibiotic resistance. Antimicrob Agents Chemother. 2013; 57: 1968-70.
Sen C, Gordillo G, Roy S, et al. Human skin wounds: A major and snowballing threat to public health and the economy. Wound Repair Regen. 2009; 17: 763-71.
Senter, A Textbook of Organic Chemistry, Fifth Ed. 1919, pp. 435-443.
Seth A, Zhong A, Nguyen K, et al. Impact of a novel, antimicrobial dressing on in vivo, Pseudomonas aeruginosa wound biofilm: quantitative comparative analysis using a rabbit ear model. Wound Repair Regen. 2014; 22: 712-9.
Shanmugam V, Couch K, McNish S, Amdur R. Relationship between opioid treatment and rate of healing in chronic wounds. Wound Repair Regen. 2017; 25: 120-30.
Sharma et al., Toluidine blue-mediated photodynamic effects on Staphylococcal biofilms. Antimicrobial Agents and Chemotherapy, 52(1):299-305, 2008.
Smith & Nephew, Inc., OTC Medication Information: Dermal Wound Cleanser, benzethonium chloride spray. Details from the FDA, via OTCLabels.com, 6 pages, retrieved Jul. 15, 2014.
Song T, Duperthuy M, Nyunt-Wai, S.Sub-optimal treatment of bacterial biofilms. Antibiotics. 2016; 5: 1-18.
Spellberg B, Srinivasan A, Chambers H. New societal approaches to empowering antibiotic stewardship. JAMA. 2016; 315: 1229-30.
Stevens D, Bisno A, Chambers H, et al. Practice guidelines for the diagnosis and management of skin and soft tissue infections: 2014 update by the Infectious Diseases Society of America. Clin Infect Dis. 2014; 59: 147-59.
Stewart P. Antimicrobial tolerance in biofilms. Microbiol Spectrum. 2015; 3: 1-30. https://www.ncbi.nlm.nih.gov/pmc/articles/PMC4507308/pdf/nihms697879.pdf. Accessed Jul. 24, 2018.
Stotts R. Wound Bioburden. In Baranoski, S, Ayello, E. eds. Wound Care Essentials: Practice and Principles. Philadelphia, PA: Wolters Klower; 2004: 121-48.
Swisher, R.D., Surfactant effects on humans and other mammals. The Soap and Detergent Association, Scientific and Technical Report, 4:1-8, 11, 16, 17,19, Nov. 1966.
Taiwanese Patent Application No. 103117207 Office Action dated Apr. 11, 2018.
Tallardia. Drug synergism: Its detection and applications. The Journal of Pharmacology and Experimental Therapeutics, 298(3):865-872, 2001.
Thomas and McCubbin, An in vitro analysis of the antimicrobial properties of 10 silver-containing dressings. The Journal of Wound Care, Sep. 2003, 12(8):105-108.
Thomas-Hess, C. Checklist for factors affecting wound healing. Adv Skin Wound Care. 2011; 24: 192.
Torkington-Stokes R, Metcalf D, Bowler P. Management of diabetic foot ulcers: valuation of case studies. Br J Nurs. 2016; 25: S27-S33.
Understanding biofilms. Bacteriality. Published online May 26, 2008. http://bacteriality.com/2008/05/biofilm/. Accessed Jul. 2, 2018.
United Nations. World Population Aging. New York. 2017. http://www.un.org/en/development/desa/population/publications/pdf/ageing/WPA2017_Highlights.pdf. Accessed Jul. 24, 2018.
U.S. Appl. No. 11/610,671 Office Action dated Apr. 2, 2008.
U.S. Appl. No. 11/610,671 Office Action dated Apr. 7, 2011.
U.S. Appl. No. 11/610,671 Office Action dated Aug. 17, 2009.
U.S. Appl. No. 11/610,671 Office Action dated Dec. 3, 2008.
U.S. Appl. No. 11/610,671 Office Action dated Feb. 18, 2010.
U.S. Appl. No. 11/610,671 Office Action dated Mar. 11, 2015.
U.S. Appl. No. 11/610,671 Office Action dated Mar. 20, 2014.
U.S. Appl. No. 11/610,671 Office Action dated Oct. 20, 2011.
U.S. Appl. No. 11/610,671 Office Action dated Oct. 8, 2014.
U.S. Appl. No. 11/610,671 Office Action dated Sep. 12, 2013.
U.S. Appl. No. 12/406,316 Office Action dated Apr. 4, 2012.
U.S. Appl. No. 12/406,316 Office Action dated Apr. 5, 2013.
U.S. Appl. No. 12/406,316 Office Action dated Aug. 10, 2011.
U.S. Appl. No. 12/406,316 Office Action dated Nov. 26, 2012.

(56) References Cited

OTHER PUBLICATIONS

U.S. Appl. No. 14/114,517 Office Action dated Aug. 13, 2015.
U.S. Appl. No. 13/990,755 Office Action dated Jan. 19, 2017.
U.S. Appl. No. 09/997,545 Office Action dated Feb. 10, 2003.
U.S. Appl. No. 09/997,545 Office Action dated Jul. 3, 2002.
U.S. Appl. No. 10/734,784 Office Action dated Apr. 4, 2007.
U.S. Appl. No. 13/124,472 Office Action dated Feb. 16, 2016.
U.S. Appl. No. 13/124,472 Office Action dated Jan. 18, 2013.
U.S. Appl. No. 13/124,472 Office Action dated Jun. 21, 2013.
U.S. Appl. No. 13/124,472 Office Action dated Jun. 4, 2015.
U.S. Appl. No. 13/124,472 Office Action dated Oct. 3, 2014.
U.S. Appl. No. 13/990,755 Advisory Action dated Jan. 2, 2019.
U.S. Appl. No. 13/990,755 Office Action dated Jun. 29, 2017.
U.S. Appl. No. 13/990,755 Office Action dated May 5, 2016.
U.S. Appl. No. 14/114,517 Office Action dated Apr. 23, 2015.
U.S. Appl. No. 14/114,517 Office Action dated Mar. 24, 2016.
U.S. Appl. No. 14/114,517 Office Action dated Oct. 20, 2016.
U.S. Appl. No. 14/654,498 Office Action dated Jul. 27, 2017.
U.S. Appl. No. 14/654,498 Office Action dated May 3, 2018.
U.S. Appl. No. 14/654,498 Office Action dated Nov. 17, 2017.
U.S. Appl. No. 14/795,176 Office Action dated Feb. 3, 2016.
U.S. Appl. N. 14/889,818 Office Action dated Feb. 26, 2019.
U.S. Appl. No. 14/889,818 Office Action dated Jan. 10, 2018.
U.S. Appl. No. 14/889,818 Office Action dated Jan. 25, 2017.
U.S. Appl. No. 14/889,818 Office Action dated Jun. 19, 2018.
U.S. Appl. No. 14/889,818 Office Action dated Jun. 9, 2017.
U.S. Appl. No. 14/889,818 Office Action dated Sep. 27, 2016.
U.S. Appl. No. 15/372,299 Final Office Action dated Nov. 9, 2018.
U.S. Appl. No. 13/990,755 Office Action dated Apr. 5, 2018.
U.S. Appl. No. 15/372,299 Office Action dated Apr. 23, 2018.
Usacheva et al., Interaction of the photobactericides methylene blue and toluidine blue with a fluorophore in Pseudomonas aeruginosa cells. Lasers in Surgery and Medicine, 40:55-61, 2008.
Varani et al., Human skin in organ culture and human skin cells (keratinocytes and fibroblasts) in monolayer culture for assessment of chemically induced skin damage. Toxicol Pathol., 35(5):693-701, 2007.
Vengerovsky, A.I., Pharmaceutical incompatibility. Bulletin of Siberian Medicine, 3:12 pages, 2003. http.7/old.ssmu.ru/bull/03/3/1684.pdf.
Wainwright. Photodynamic antimicrobial chemotherapy (PACT). Journal of Antimicrobial Chemotherapy, 42:13-28, 1998.
Wainwright et al., The Use of new methylene blue in Pseudomonas aeruginosa biofilm destruction. Biofouling, 18:247-249, 2002. (Abstract only).
Walker M, Bowler P, Cochrane C. In vitro studies to show sequestration of matrix metalloproteinases by silver-containing wound care products. Ostomy Wound Manage. 2007; 53: 18-25.
Walker M, Metcalf D, Parsons D, Bowler P. A real-life clinical evaluation of a next-generation antimicrobial dressing on acute and chronic wounds. J Wound Care. 2015; 24: 11-22.
Waring et al. Physico-chemical characterisation of carboxymethylated spun cellulose fibres. Biomaterials 22:903-912 (2001).
Webb R. A chronic case of confusion. J of Wound Care. 2017; 26: 421.
Welsby S. The Spectrum Activity of AQUACEL Ag+ with Strengthening Fibre Ribbon using an In Vitro Corrected Zone of Inhibition Assay. 2015. ConvaTec data on file.
White, "An historical overview of the use of silver in wound management," Actisorb Silver 220, The Silver Supplement Part Two: Clinical Evidence, 6(Supp. Pt. 2): 6 pages (2001).
Wilkinson H, Stephenson C, Hardman M. Comparing the effectiveness of polymer debriding devices using a porcine wound biofilm model. Adv Wound Care. 2016; 5: 475-85.
Wirtanen, et al., Performance Evaluation of disinfectant Formulations Using Poloxamer-hydrogel Biofilm-constructs, Journal of Applied Microbiology, 85:965-971, 1998.
Wolcott R. Biofilms cause chronic infections. J of Wound Care. 2017; 26: 423-5.
Wolcott R. Disrupting the biofilm matrix improves wound healing outcomes. J Wound Care. 2015; 24: 366-71.
Wolcott R, Rhoads D. A study of biofilm-based wound management in subjects with critical limb ischemia. J Wound Care. 2008; 17: 145-55.
Wolcott R, Sanford N, Gabrilska R, Oates J, Wilkinson, J, Rumbaugh K. Microbiota is a primary cause of pathogenesis of chronic wounds. J Wound Care. 2016; 25: Sup10: S33-S43.
Wood et al., Erythrosine is a potential photosensitizer for the photodynamic therapy of oral plaque biofilms. Journal of Antimicrobial Chemotherapy, 57:680-684, 2006.
Zölß C, Cech JD. Efficacy of a new multifunctional surfactant-based biomaterial dressing with 1% silver sulphadiazine in chronic wounds. Int Wound J. 2016; 13: 738-43. doi: 10.1111/iwj.12361.
Canadian Office Action, Canadian Intellectual Property Office, Canadian Patent Application No. 2,819,303, dated Oct. 30, 2018, 4 pages.
Japanese Search Report, Japan Patent Office, Japanese Patent Application No. 2018-128781, dated May 28, 2019, 12 pages.
Japanese Office Action, Japan Patent Office, Japanese Patent Application No. 2018-128781, dated Nov. 26, 2019, 3 pages.
Canadian Office Action, Canadian Intellectual Property Office, Canadian Patent Application No. 2,819,303, dated Nov. 28, 2019, 3 pages.
Japanese Pre-Appeal Examination Report, Japan Patent Office, Japanese Patent Application No. 2018-1128781, dated Aug. 6, 2020, 2 pages.
Notification of Reasons for Refusal, Japan Patent Office, Japanese Patent Application No. 2018-128781, dated Dec. 1, 2020, 5 pages.

* cited by examiner

COMPOSITION FOR DETECTING BIOFILMS ON VIABLE TISSUES

CROSS-REFERENCE

This application is a continuation application of Application No. 13/990,755, filed Feb. 19, 2014 which is a U.S. National Phase of International Application No. PCT/GB2011/001665, filed on Nov. 30, 2011, designating the United States of America and published in the English language, which is incorporated herein by reference in their entirety and to which application we claim priority under 35 USC § 120.

This invention relates to a composition which can be applied to viable tissues such as chronic wounds (e.g. leg ulcers, pressure ulcers, diabetic foot ulcers), acute wounds (e.g. cuts, abrasions, burns), skin and bone for the detection of microbial biofilms as an early warning indicator for tissue at risk of infection. More particularly the invention relates to a composition capable of making biofilms on viable tissues observable while at the same time avoiding wound and skin irritation and retardation of healing. A further embodiment of the invention relates to a kit for use in the detection of biofilms on viable tissues.

Viable tissues are often colonised by a variety of microorganisms, some of which may cause infection. It is becoming increasingly accepted that chronic and acute wound healing is impaired by the presence of microorganisms colonising the wound. Compelling evidence is emerging that these microorganisms may exist in wounds primarily in the form of biofilms. During colonisation, bacteria and other microorganisms such as yeasts and fungi, attach firmly to tissue and form biofilm via the secretion of an extracellular matrix of polymeric substances. This mode of growth imparts a degree of protection to microorganisms within the biofilm in the form of physical protection from topical and systemic antimicrobial agents due to the surrounding matrix. It is also thought that microorganisms within biofilms have altered phenotypes and genotypes compared to their free-swimming, planktonic counterparts. Biofilm microorganisms are known to be metabolically less active, and as such this may also provide a degree of resistance to traditional antimicrobial approaches such as antibiotics, which are known to work against metabolically-active bacteria. Furthermore, the presence of biofilms in wounds also impedes the host immune system in the inflammatory microbial clearance, and the granulation and re-epithelialisation phases, of the normal wound healing process.

Consequently, there is a need to develop methods or devices to rapidly detect the presence of biofilm in viable tissues before and after selected treatment protocols. This would help researchers to understand if microorganisms live in the biofilm state on skin and in wounds, and to allow them to follow maturation or clearance of such biofilm communities. A biofilm detection method or device would also allow researchers to develop effective anti-biofilm strategies and effective wound healing protocols of care, and in clinical practice, it would guide selection of appropriate wound dressings and aid the monitoring of the effectiveness of a treatment protocol given by the wound care practitioner.

Biofilms are typically comprised of bacteria encased within an exopolymeric substance (or matrix) that consists of long-chain polysaccharides with complex linkages such as 1,3- or 1,4-β-linked hexose linkages (examples of some common biofilm polysaccharides are teichoic acid, ketal-linked pryruvates N-acetylglucosamine, and the uronic acids: D-guluronic, D-galacturonic and mannuronic acids), protein (of which some may play a structural role), DNA (extracellular, some of which may have a structural role), lipids, metal ions ($Ca^{2+}$, $Mg^{2+}$, $Fe^{3+}$, etc.) and water. Biofilms may also be associated with devitalised host tissues such as slough and necrotic tissue.

Biofilm extracellular polymeric substances (EPS) are also referred to as biofilm extracellular matrix or bacterial-derived tissue. Whilst biofilm is mainly water by weight and bacteria may only comprise 10-20% of the volume of biofilm, EPS constitutes the majority of the biomass/dry weight of biofilm.

Biofilms such as those found on teeth in the form of dental plaque, are often easy to visualise with the naked eye due to their thickness, colour and the nature of the substrate on which they form. Biofilm visualisation in, for example, a chronic or acute wound is not straightforward due to the colours present in the wound and the contents of the wound. Chronic and acute wounds are usually complex in terms of containing dead or devitalised tissue (slough), exudate, pus, blood, medicaments, dressing components, in addition to bacteria and biofilm. As such it may be difficult to detect the presence of a biofilm in a wound as the visualisation of wound biofilms by the naked eye is difficult. There is thus a need for a means to aid detection of the biofilm for instance by a composition which is able to preferentially stain wound biofilms so that they can be visualised. Once visualised, the biofilm can be treated appropriately.

Surprisingly we have found that it is possible to preferentially stain biofilms by the use of a composition comprising a stain which allows the detection of biofilm.

Accordingly a first aspect of the invention provides a staining composition for use in making biofilm on viable tissue detectable wherein the composition preferentially stains the biofilm and comprises a coloured or fluorescent staining agent in solution in a quantity effective to stain said biofilm and render it detectable.

Preferably the biofilm is made detectable by the naked eye or in conjunction with illumination and/or optical devices.

Preferably the staining agent is a dye which will selectively bind to EPS/bacteria and not to host viable tissue. The staining agent should not significantly stain non-biofilm components in, for example, a chronic or acute wound, such as wound tissue, surrounding skin, slough (dead or devitalized tissue), exudate, blood, pus, inflammatory cells (neutrophils, macrophages), cells involved in the healing process (fibroblasts, endothelial cells, keratinocytes), or medicaments or dressing components that may remain in the wound. Such a staining agent would preferably be a molecule of the required size and structure; for example, a low molecular weight, compact, planar molecule that is capable of diffusion through EPS and bacterial cell membranes. The staining agent may have anionic groups to give colour and possibly fluorescent properties; and may have cationic groups for charge interactions with negatively-charged biofilm EPS polysaccharides and bacterial cell walls. These charged groups should preferably be permanent charges so that they are not affected by the pH of applied formulations or the viable tissue/biofilm environment.

Such a staining agent is preferably of a suitable colour or brightness that it may be possible to observe the stained biofilm directly with the naked eye. However, due to the complex and highly pigmented nature of wounds some colours of stain might be difficult to observe. For example, in necrotic wounds, sloughy wounds, or bleeding wounds there may be hues of black, brown, red, yellow, etc. Whilst blue or green dyes may be considered preferable here, they may appear dark or black if located adjacent to or on brown, red or yellow-coloured tissue. Rather than relying solely on the observer being able to detect the stain with the naked eye, it is preferable to use a stain that can fluoresce so that it is more readily detectable. Many classes of compounds that are potential staining agents are also fluorescent, in that they are capable of absorbing photons of light of certain wavelengths and becoming electronically excited, emitting this light energy in the form of fluorescence. It is possible to detect such fluorescence using light filters that are tailored to the fluorescence emission spectra of relevant molecules so that the observer only views a narrow spectral band that corresponds to the wavelengths of fluorescence. For example, lenses with specific optical filters, such as those used in laser safety, could be used in conjunction with an appropriately-specific light source to detect fluorescence, thereby allowing detection of biofilm on viable tissues. This method of biofilm detection may have advantages over detection using the naked eye in that fluorescent detection is possible even for very thin biofilms, which may be only a few layers of microbial cells thick and does not rely solely on the stain itself being visible.

By preferentially staining it is meant that the staining agent selectively binds to the biofilm rather than the host viable tissue. In this way, the staining agent can be used simply to detect the biofilm by revealing the presence and location the biofilm. The staining agent becomes bound or adsorbed to extracellular biofilm matrix molecules as well as being bound or adsorbed to and/or taken up by the biofilm bacteria cells rather than the tissue of the wound. Preferably the staining of the biofilm by the staining agent reveals the presence of biofilm by making it detectable to the naked eye. For some staining agents the stained biofilm can be made to fluoresce, for instance by illumination with a light source. The fluorescence can make the stained biofilm more visible. The light source is selected to emit light of an appropriate wavelength such that the staining agent absorbs light energy in the form of photons to excite the staining agent and cause it to fluoresce. The observation of fluorescence may be enhanced using appropriate optical filters which exclude non-fluorescent wavelengths for the staining agent, for instance in the form of optically-filtered lenses.

The compositions according to a first aspect of the invention comprise one or more staining agents capable of preferentially staining biofilms. Preferably the staining agent is a dye, the biofilm-staining dye absorbing maximally in the visible region, more preferably 380 nm to 720 nm and even more preferably 500 nm to 600 nm, as this makes a wide range of light sources suitable for use with the composition of the invention or for inclusion in the kit of the invention.

Preferably the staining agent produces sufficient fluorescence for detection, such that a wavelength range suitable for excitation and a distinct and higher wavelength range suitable for fluorescence emission detection can be delivered from illumination devices and detected using optically-filtered lens devices.

Staining agents suitable for use in compositions of the invention are most preferably selected from those based upon organic chemical compounds, more likely to be those containing aromatic ring structures, for example benzene, or extended conjugation, for example in porphyrin or pheophorbides, more likely those with fused polycyclic hydrocarbons, for example naphthalene, anthracene, phenanthraline and pyrene, and most likely those also containing heterocyclic aromatic structures where the heterocyclic atom or atoms are oxygen, nitrogen or sulphur, or a mixture thereof, for example furan, thiophene, pyrrole, pyran, pyridine and oxazine.

These staining agents may also display the properties of fluorescence. Most appropriate are those that absorb and emit light of wavelengths in the visible electromagnetic spectrum (380 nm-720 nm). Such agents are likely to have chemical structures that contain an extended region of conjugation, for example fluorone and its derivatives (alternatively known as xanthenes and rhodamines) such as eosin, erythrosine, Rose Bengal, fluorescein-5-isothiocyanate, 5-chloromethyl fluorescein, 6-carboxy fluorescein, 2,7-Bis-(carboxy ethyl)-5(6)-carboxy fluorescein; Rhodamine B, Rhodamine 6 G, Rhodamine 123, Rhodamine iodoacetamide, Sulphorhodamine B, Sulphorhodamine 101, tetramethyl rhodamines or Texas Red. Derivatives of cyanine such as 3,3'-dihexadecylindocarbocyanines, 3,3'-dipropyloxadicrbocyanine, aluminium phthalocyanine disulphonate, aluminium tetrasulphophthalocyanine, aluminium phthalocyanines, zinc phthalocyanines, napthalocyanines, or the mucopolysaccharide stain Alcian Blue. Acridine and its derivatives such as Acriflavine, Aminacrine, 2-aminoacridine or 9-aminoacridine. Finally, appropriate agents may come from the classes of oxazine derivatives such as Nile Blue, Nile Red, Fura Red or Fura-2; quinolone and its derivatives; adenosine derivatives such as 2'3'-O-(2,4,6-trinotro-cyclohexadienylidine)adenosine 5'-triphosphate or 3'-O—(N-methylanthraniloyl)adenosine 5'-triphosphate; triarylmethanes such as Patent Blue V, Crystal Violet, Brilliant Blue or Fast Green; 5 phenothiaziniums such as Methylene Blue or Toluidine Blue O and its derivatives such as 1-methyl methylene blue or 1,9-dimethyl methylene blue; phenanthridine derivatives such as ethidium or hydroethidine; pheophorbide derivatives such as sodium pheophorbide; and porphyrin derivatives such as chlorin e6, benzoporphyrin derivatives, porphines, 10 meso-tetra porphines, hematoporphyrins or protoporphyrins.

The staining agent is preferably included in the composition at a level of from 0.0001% to 1% by weight, more preferably 0.0025% to 0.025% by weight, even more preferably 0.0025% to 0.01% by weight.

The compositions of the present invention may be in a form that lightly adheres to tissues and may be readily rinsed away after a short duration to aid visualisation of the stained biofilm. A viscous fluid, for instance a water- or glycerol-based gel (in the form of a gel applicator, spray or sheet), foaming mousse, cream or ointment would give intimate contact with a wound bed. Alternatively, a thin, soluble, cast film or a lyophilized, dissolving wafer could be used to provide intimate contact with a wound bed. In any such delivery system the formulation preferably should be easily rinsed away from viable tissues using a standard irrigant such as saline, for a few seconds.

In gel form, the composition may also comprise a viscosifier such as a cellulose derivative such hydroxyethyl cellulose (HEC), carboxymethyl cellulose or hydroxypropyl cellulose; gums; sugar/alcohol derivatives such as glycerol, sorbitol, maltitol, mannitol, maltodextrin or polydextrose; natural polymers such as gelatin, pectin, chitosan or alginate; synthetic polymers such as carbopol, polyvinylpyrolidone, polyvinyl acetate, polyvinyl alcohol, polyacrylate, polymethacrylate, polyethylene glycol or poloxamers. Preferably the composition in gel form may comprise from 1 to 5% by weight of a viscosifier and most preferably HEC.

The composition of the invention may be in gel form and may also comprise a humectant such as propylene glycol (PG), glycerol, polyethylene glycol, polydextrose, sorbitol, triethanolamine, cyclomethicone, ammonium lactate or glycerol ester. Preferably the composition comprises from 5% to 15% by weight of a humectant and most preferably PG.

Preferably the composition of the invention comprises excipients to optimise binding of the stain to biofilm. For instance, the composition of the invention may also comprise a metal chelating agent such as tetra sodium ethylene diamine tetraacetic acid (EDTA), citric acid, deferasirox, deferiprone, deferoxamine, deferazoxane, ethylene glycol tetraacetic acid, gluonic acid, nitrilotriacetic acid or trisodium citrate at a level of 0.1 to 2.0% by weight, or an agent to assist penetration of the staining agent into the biofilm such as a surfactant for example Tween 80, Span 20, or coamidopropylbetaine (CAPD) and in particular a cationic quaternary ammonium surfactant such as dialkyl dimethyl ammonium chloride, alkyl pyridinium chloride, benzalkonium chloride (BaCl), benzethonium chloride (BeCl), disodium cocamphodiacetate, cetyl morpholinium ethosulphate or an alkyl trimethyl ammonium chloride at a level of 0.1 to 1.0% by weight. The addition of a surfactant may also act as a foaming agent. For example, the surfactants BeCl, Tween 80, Span 20, CAPD, sodium $C_{14-16}$ olefin sulfonate or Softisan 649 can act as foaming agents to give the formulation characteristics of a foaming mousse.

Preferably the composition of the invention has a pH in the range of from 5 to 7 and most preferably around 5.5.

Preferably the composition of the invention is in the form of a viscous fluid and comprises a viscosifier such as HEC, a humectant such as PG, a metal chelator such as EDTA, a surfactant such as BeCl and water and in particular 2.0% w/v hydroxyethylcellulose, 10.0% w/v propylene glycol, 0.5% EDTA, 0.5% BeCl and approximately 87% v/v sterile, distilled water. Alternatively, the compositions of the present invention could be in the form of a solution applied to the wound from a syringe, sachet, spray bottle, aerosol bottle, non-propellant pump bottle, brush or a gel sheet, film or dissolving wafer.

The formulation could be terminally sterilized by autoclaving or gamma irradiation. Alternatively, the formulation could be a preserved solution containing, for example preservatives such as DMDM hydantoin or parabens such as methyl-, ethyl- or propyl-paraben.

The composition of the present invention will be used primarily on viable tissues which show signs of clinical infection (inflammation, malodour, purulent exudate, hypoxia, etc.), may be at risk of infection, appear to have slough (host-derived tissue) or biofilm (bacteria-derived tissue) present, or are generally recalcitrant. The composition could also be used at dressing change, in order to detect biofilm, and also to monitor the efficacy of the treatment regime and direct future treatment via the reduction in detected biofilm.

A further aspect of the present invention relates to a kit of parts for use in the detection of biofilms on viable tissue, the kit comprising:
  a composition comprising a staining agent which preferentially stains biofilms and
  a light source capable of causing the staining agent to fluoresce.

Preferably the kit further comprises optical filters to enable the specific detection of fluorescence in the form of spectacles or integrated optical filters.

The light source may be a white light source such as tungsten, halogen or pulsed xenon lamp that is passed through a "short pass" filter. Preferably the light source is a monochromatic or narrow spectrum source that does not require filtering or attenuation such as a light emitting diode with an output that closely correlates with the spectral characteristics of the staining agent. As such the light source is preferably small, portable, hand-held and generates no or negligible heat. The light source may be multiple use or fully disposable.

Preferably the kit further comprises spectacles, or the light source contains an integrated lens, for use in detecting the biofilm wherein the spectacles or lens contain a filter to exclude all wavelengths of light below the absorption maxima ($Abs_{max}$) of the staining agent. In this way the user is assisted in detecting the fluorescence of the staining agent present in the biofilm. More preferably the spectacles or lens filter is efficient at transmitting wavelengths of light corresponding to the fluorescence emission spectra of the staining agent. The spectacles can be multiple use or fully disposable (in the same way that an integrated lens in the light source could be).

Preferably the kit further comprises a wound irrigation solution for rinsing the viable tissue before and/or after illumination with the light source.

In an example of typical use, a composition according to the invention is applied to the whole wound or desired regions in order to achieve a thin but consistent layer of composition for instance 0.1 to 0.5 cm in thickness. The composition is left in place for 0.1 to 15 minutes, more preferably 0.5 to 2 minutes. Prior to any illumination, the formulation can be left in place or more preferably excess formulation is rinsed away from the wound using a suitable wound irrigation solution. Rinsing the excess formulation away can enable the staining to show where the biofilm is in the wound so that these areas can be treated for example by curette.

The wound is then inspected for presence of preferentially stained biofilm. This may be done with the naked eye or the wound can be illuminated with a light source at a distance in the range of 1 to 50 cm. Preferably the light source is at a distance of 5 to 20 cm. The light source spectral output is selected to correspond to the fluorescence emission spectra of the staining agent; for example, for Rose Bengal, which has a fluorescence maxima of 575 nm, a suitable light source might emit wavelengths of 550-600 nm. This causes the agent in the stained biofilm to fluoresce. Preferably the user wears spectacles to observe the wound or observes the wound through an integrated lens in the light source. The spectacles or lens have a light filtration system which excludes wavelengths of light below the fluorescence emission range of the staining agent and allows any fluorescence to be seen remarkably clearly and specifically and thus, detection of any biofilm present.

Typically, treatment should take place at subsequent dressing changes. The wound can be further inspected for presence and reduction of biofilm with the naked eye or with the light source and spectacles or integrated lens. The wound can then be dressed with an appropriate primary and secondary dressing.

The following examples are illustrative of the present invention.

Example 1

Assessment of Biofilm Stains using the Constant-Depth Biofilm Fermenter

A constant depth biofilm fermenter (CDFF) was used to culture 4-day mixed biofilms of *Staphylococcus aureus* and *Pseudomonas aeruginosa*. Briefly, biofilms were formed in recesses in 15 PTFE pans around the rim of a rotating steel turntable onto which inoculum or sterile growth media was allowed to steadily drip. A scraper bar distributed bacterial inoculum or media over the pans as the turntable rotated, maintaining the biofilms at a steady depth. Each pan contained 5 removable plugs, 4 mm in diameter which were recessed to a depth of 300 µm. The resulting biofilms that grew in the plug recesses were reproducible in terms of appearance and microbiological composition and could be removed from the CDFF through a sampling port using sterile instruments. In duplicate, biofilm-containing pans were removed from the CDFF, rinsed once by dipping in sterile saline for 5 seconds, then incubated in 10 ml volumes of the following potential biofilm stains at 100 µM concentration in deionised water unless stated, in the dark for two minutes: Erythrosine; Rose Bengal; Fast Green; Rose Bengal with 2% w/v EDTA and 1% w/v benzalkonium chloride (BaCl) (RBEB); Rose Bengal with 2% w/v tetra sodium EDTA and 1% w/v benzalkonium chloride in a 2% w/v hydroxyethyl cellulose and 10% w/v propylene glycol gel (Gel-RBEB). Following another rinse in saline, six plugs for each stain were incubated overnight at 37° C. in 6 ml volumes of 2% sodium dodecyl sulphate (SDS) in water for digestion. Samples were then spun at 13,000 rpm for 10 minutes to separate the supernatant from digested cell debris. Absorption spectra of the aspired supernatants were then measured in a spectrophotometer and these spectra compared to spectra of known concentrations (100 µM) of each stain in 2% SDS.

Figure 1:
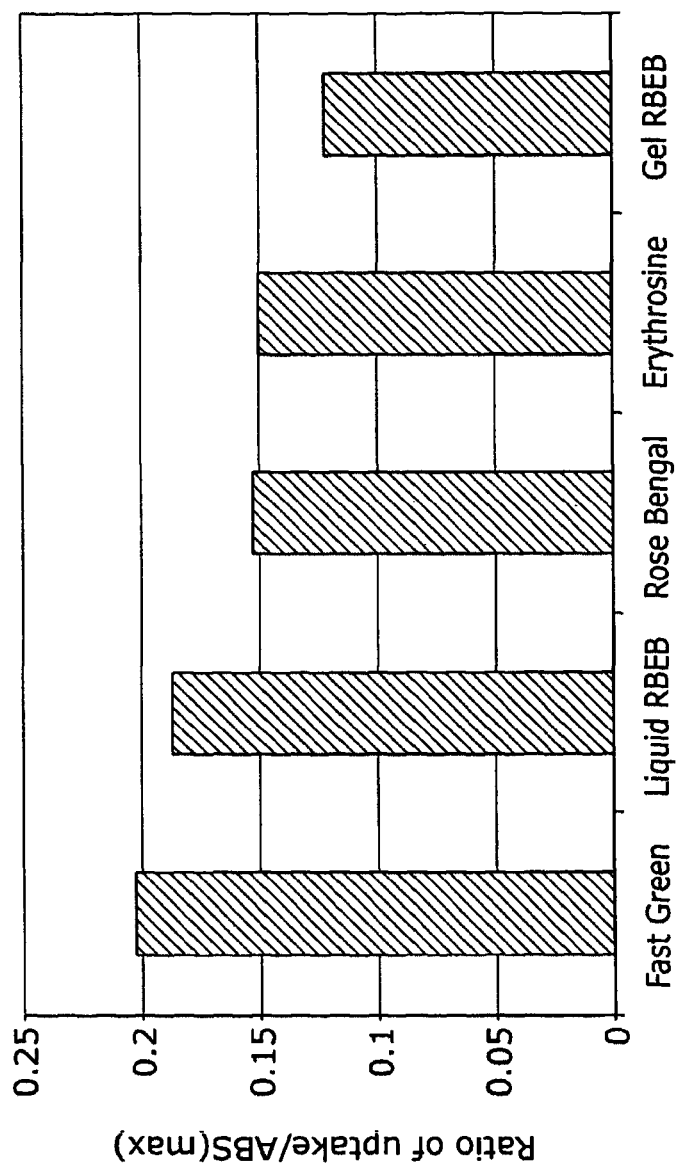
FIG. 1. Initial screening of selected dyes as biofilm stains using biofilms grown in the CDFF (n=6).

FIG. 1 shows that Fast Green appeared to be the most effective stain of biofilms grown in the CDFF, closely followed by Rose Bengal with EDTA and BaCl in liquid form. The addition of the EDTA and BaCl excipients appeared to enhance the uptake of Rose Bengal into the biofilms.

Example 2

Assessment of Biofilm Stains using the CDC Biofilm Reactor

A Centre for Disease Control (CDC) biofilm reactor was used to culture 48 hour mixed biofilms of *Staphylococcus aureus* and *Pseudomonas aeruginosa*. Briefly, biofilms were formed on coupons on reactor rods which were held within the reactor vessel containing a continuously mixed culture of *S. aureus* and *P. aeruginosa* at 35° C. Biofilm-containing coupons were removed from the rods, rinsed once by dipping in sterile saline for 5 seconds, then incubated in 10 ml volumes of the following biofilm stains at 100 µM concentration in deionised water, in the dark for two minutes: Erythrosine; Rose Bengal; Alcian Blue; Rhodamine B; Rhodamine 123; Rose Bengal with 2% w/v EDTA and 1% w/v BaCl (RBEB). Following another rinse in saline, nine coupons for each stain were each added to 2 ml volumes of 2% SDS for stomaching at 'high' setting for 1 minute then incubated overnight in the dark at 37° C., for digestion. Samples were then spun at 13,000 rpm for 5 minutes to separate the supernatant from digested cell debris. Absorption spectra of the aspired supernatants were then measured in a spectrophotometer and these spectra compared to spectra of known concentrations (100 µM) of each stain in 2% SDS.

Figure 2A:
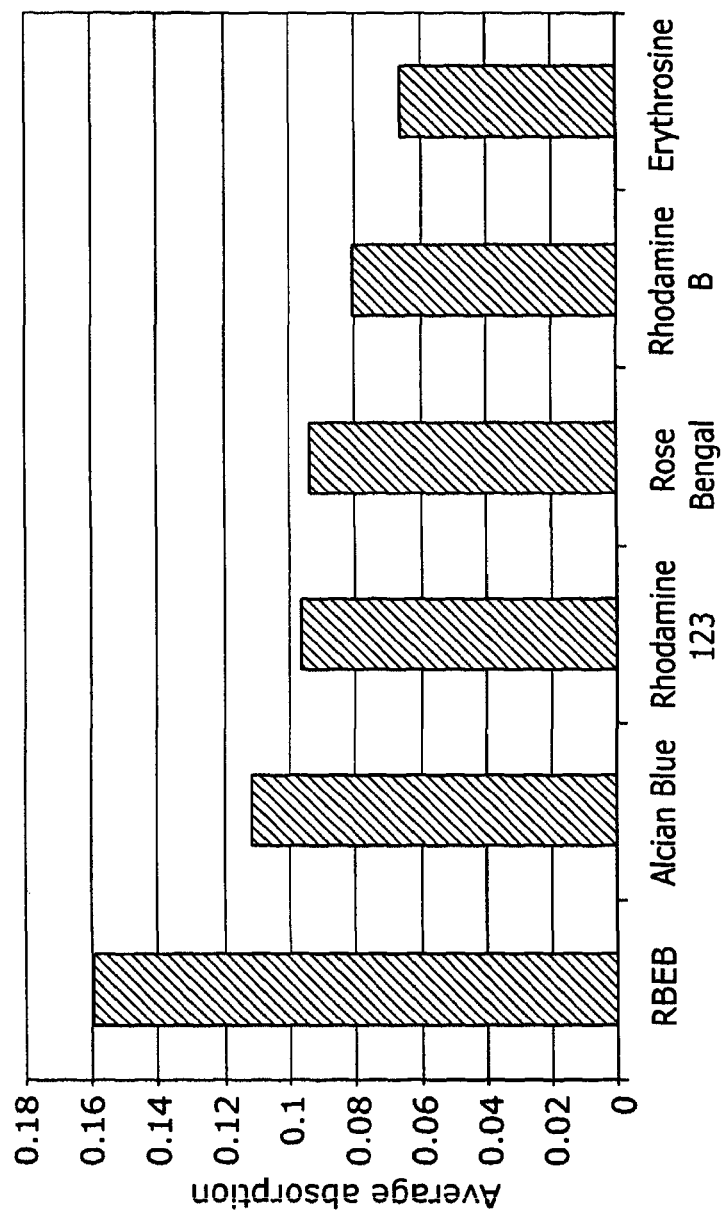
FIG. 2a. Screening of selected dyes as biofilm stains using biofilms grown in the CDC biofilm reactor (n=9). Absorption data.
Figure 2B:
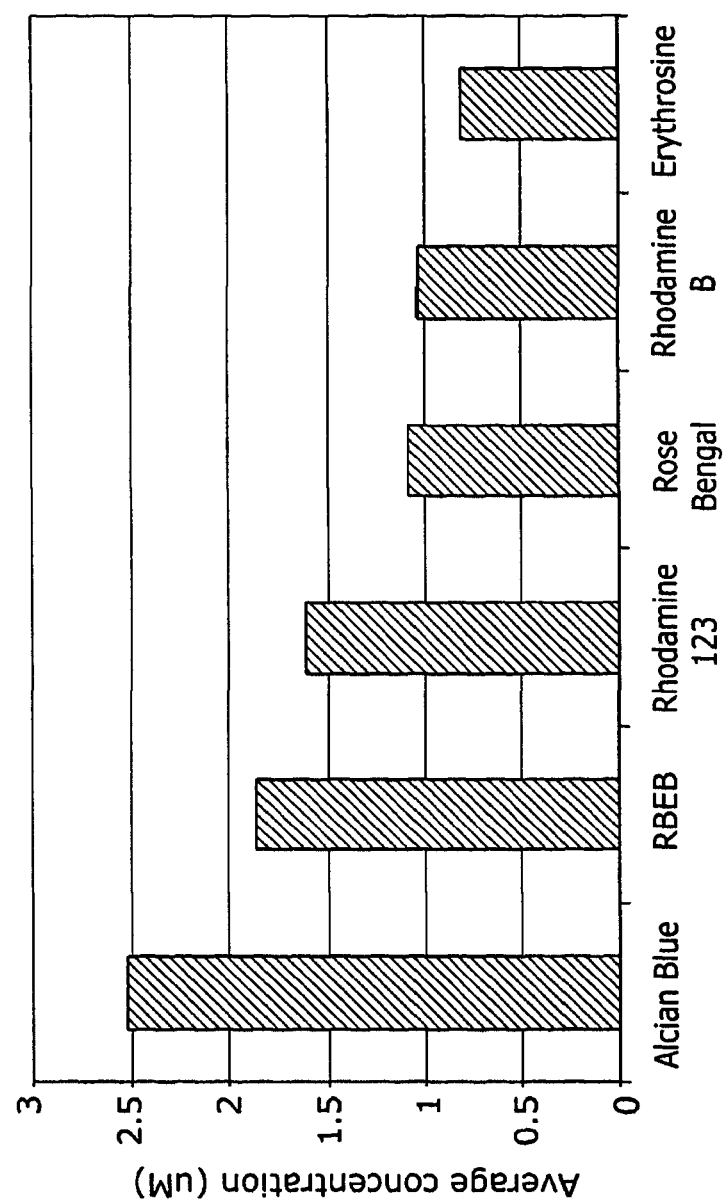
FIG. 2b. Screening of selected dyes as biofilm stains using biofilms grown in the CDC reactor (n=9). Concentration data.

FIG. 2a shows how in terms of absolute absorption or 'brightness', RBEB was the most efficient biofilm stain, followed by the carbohydrate stain, Alcian Blue. The EDTA and/or BaCl appeared to enhance the uptake of Rose Bengal by more than 60%. When the same data was expressed as a ratio of measured absorption: absorption at 100 1.1M (i.e. concentration), Alcian Blue appeared to be the most effective biofilm stain.

Example 3

Assessment of Biofilm Stains using a Pork Belly Biofilm Model

Figure 3:
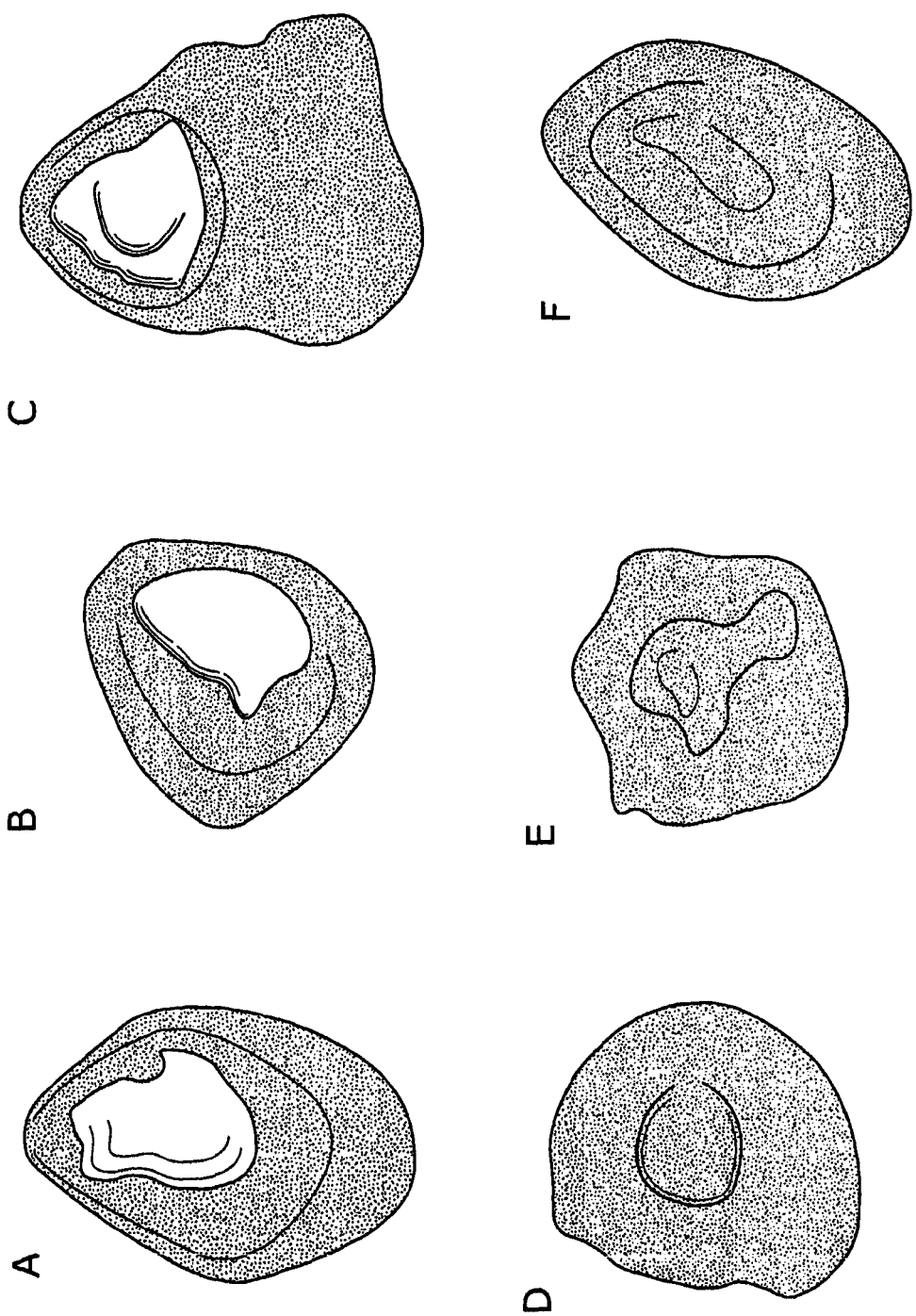
FIG. 3. Rose Bengal with EDTA and BaCl (RBEB) stained (A-C) and control (D-E) samples of meat containing mixed *S. aureus* and *P. aeruginosa* biofilms.

A pork belly biofilm model was used to further assess biofilm stains. Pieces of pork belly were cut using a 20 mm bore and a 6 mm borer was used to create indentations in the centre of the samples. Samples were then sterilized by gamma irradiation. Samples were inoculated with 10 µl volumes of a ~1×10$^7$ cfu/ml mixed suspension of *S. aureus* and *P. aeruginosa* then incubated at 35° C. in Parafilm-sealed Petri dishes for 72-96 hours. Samples that appeared to have visible biofilms in the central bore hole only were then stained by dipping the samples into 10 ml volumes of 100 µM Rose Bengal with 2% w/v EDTA and 1% w/v BaCl (RBEB) for two minutes with rinsing in saline before and after staining. Control samples were not stained and therefore only dipped in saline for 2 minutes. Samples were then photographed, examples of which are shown in FIG. 3. The three samples (AtoC) shown that were stained with RBEB clearly demonstrate the selective uptake of the stain by the biofilms which were contained within the indentations. The three control samples show that without this staining it is difficult to ascertain if and where biofilm is present in the samples.

Example 4

Rose Bengal Staining of Biofilms Crown using a Membrane Filter Biofilm Model

Figure 4:
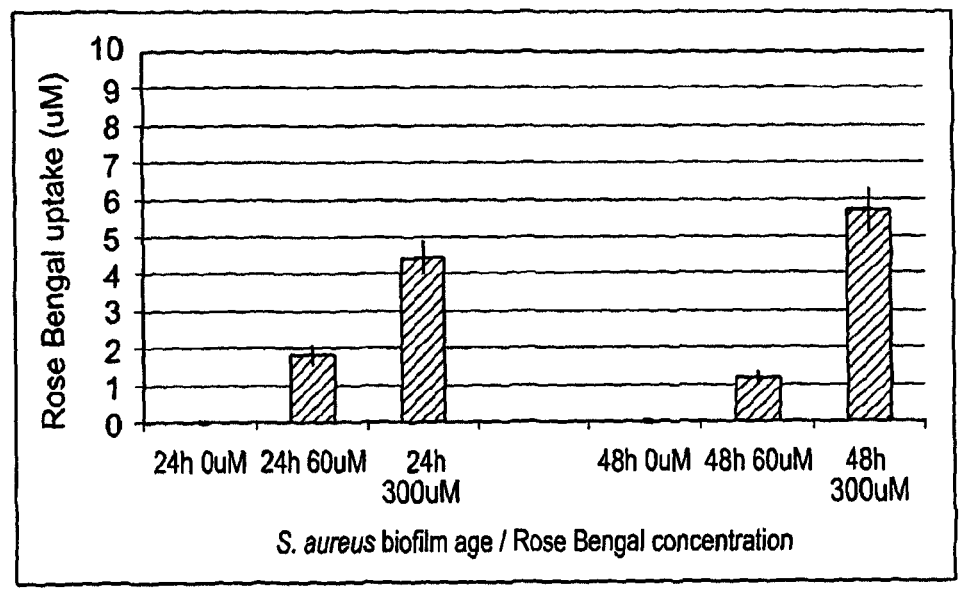
FIG. 4. *S. aureous* biofilm age vs dye concentration.
Figure 5:
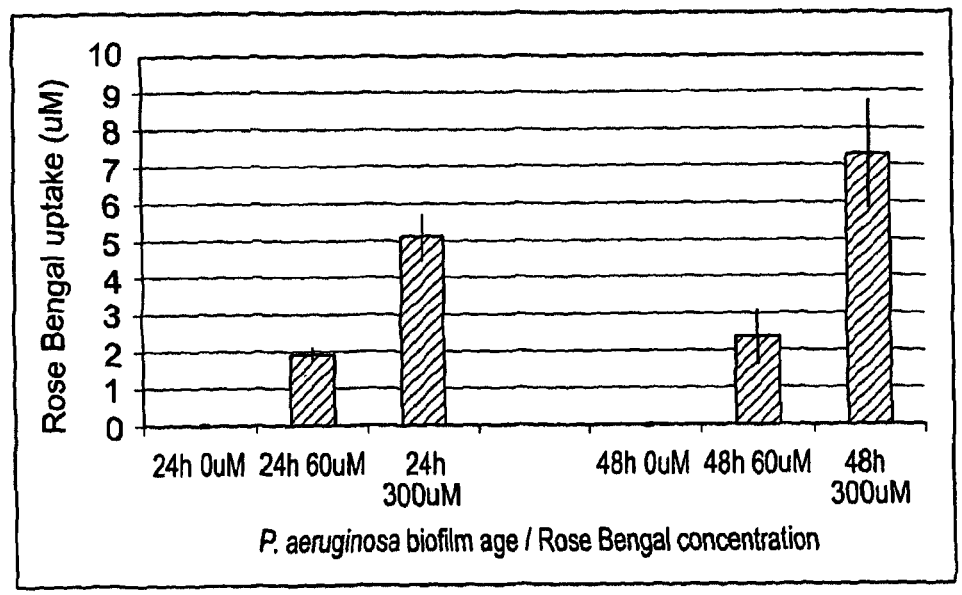
FIG. 5. *P. aeruginosa* biofilm age vs Rose Bengal concentration.

A membrane filter biofilm model was used to study the effect of Rose Bengal concentration on the efficacy of biofilm staining. Briefly, a 5 µl volume of a 5×10$^5$ cfu/ml suspension of *S. aureus* or *P. aeruginosa* was added to the centre of sterile membrane filter discs (pore size 0.2 µm; Anodisc, Whatman) which were placed onto 7 ml volumes of sterile Tryptic Soya Broth in lidded 6-well plates. Samples were incubated for 4 hours (immature biofilms), and 24 and 48 hours (mature biofilms), and excess planktonic cells were rinsed from the filters. The biofilms on the filters were stained by pipetting 2 ml volumes of Rose Bengal (60 µM or 300 µM) or saline (negative control) for 30 seconds, followed by rinsing. Rose Bengal was recovered from the biofilm samples by stomaching and overnight digestion in 2% sodium dodecyl sulphate, centrifugation, then measuring of absorption spectra in a UV-vis spectrophotometer. Rose Bengal uptake per sample was determined by comparison of absorption values with a standard curve of Rose Bengal in 2% SDS. Tables 1 and 2 show that mature *S. aureus* and *P. aeruginosa* biofilms took up Rose Bengal in a dye concentration- and biofilm age-dependent manner. Only at the highest concentrations of 300 μM did the immature, 4-hour biofilms appear to be stained, although this was likely due to some staining of the filters themselves. FIGS. 4 and 5 show how mature, 48-hour biofilms of *S. aureus* and *P. aeruginosa* took up more Rose Bengal than 24-hour biofilms, and also that 300 μM Rose Bengal resulted in significantly more staining of the biofilms than 60 μM Rose Bengal. This simple method for quantifying the uptake of Rose Bengal by biofilms utilises the absorption spectra of the dye. Using the absorption spectra to quantify the dye is similar to detecting the fluorescence using a light source with optical filters. Uptake could then alternatively be observed qualitatively using the naked eye or by observing the fluorescence emission of the Rose Bengal in conjunction with a light source and optical filter.

TABLE 1

| Age (h) | [RB] (μM) | 1 | 2 | 3 | Avg | S.D. |
|---|---|---|---|---|---|---|
| 4 | 0 | 0 | 0 | 0 | 0 | 0 |
| 4 | 60 | 0 | 0 | 0 | 0 | 0 |
| 4 | 300 | 1.59 | 1.45 | 1.64 | 1.56 | 0.10 |
| 24 | 0 | 0 | 0 | 0 | 0 | 0 |
| 24 | 60 | 1.66 | 1.72 | 2.17 | 1.85 | 0.28 |
| 24 | 300 | 4.82 | 4.55 | 3.95 | 4.44 | 0.45 |
| 48 | 0 | 0 | 0 | 0 | 0 | 0 |
| 48 | 60 | 1.22 | 1.12 | 1.37 | 1.24 | 0.12 |
| 48 | 300 | 6.26 | 5.18 | 5.71 | 5.72 | 0.54 |

TABLE 2

| Age (h) | [RB] (μM) | 1 | 2 | 3 | Avg | S.D. |
|---|---|---|---|---|---|---|
| 4 | 0 | 0 | 0 | 0 | 0 | 0 |
| 4 | 60 | 0 | 0 | 0 | 0 | 0 |
| 4 | 300 | 1.52 | 1.76 | 1.88 | 1.72 | 0.18 |
| 24 | 0 | 0 | 0 | 0 | 0 | 0 |
| 24 | 60 | 2.04 | 1.76 | 2.02 | 1.94 | 0.15 |
| 24 | 300 | 5.0.5 | 5.84 | 4.41 | 5.10 | 0.72 |
| 48 | 0 | 0 | 0 | 0 | 0 | 0 |
| 48 | 60 | 3.15 | 1.66 | 2.37 | 2.39 | 0.74 |
| 48 | 300 | 6.20 | 9.01 | 6.69 | 7.30 | 1.50 |

The invention claimed is:

1. A staining composition for use in making biofilm detectable on viable tissue that preferentially stains the biofilm rather than the viable tissue, the composition comprising:
    a staining agent in a quantity effective to stain the biofilm and render the biofilm detectable, wherein the staining agent is Rose Bengal,
    0.1 to 2.0% by weight EDTA,
    0.1 to 1.0% by weight of a surfactant, and
    a preservative in the form of methyl-paraben to provide preservative action in the composition,
    wherein the composition is a non-gelled composition, and wherein the composition is in the form of a lyophilized wafer.

2. A composition as claimed in claim 1, wherein the composition preferentially stains the biofilm by selectively binding to the biofilm rather than the viable tissue.

3. A composition as claimed in claim 1, wherein the composition allows detection of the biofilm by preferentially staining and revealing to the naked eye.

4. A composition as claimed in claim 1, wherein the composition allows detection of the biofilm by preferentially staining the biofilm with a staining agent which is capable of fluorescence.

5. A composition as claimed in claim 1, wherein the staining agent absorbs light of wavelengths from 380 nm to 720 nm.

6. A composition as claimed in claim 1, wherein the composition allows the detection of the biofilm by preferentially staining and revealing the biofilm when the biofilm is illuminated with light including wavelengths that cause the biofilm to fluoresce.

7. A composition as claimed in claim 6, wherein the fluorescence is detectable with the naked eye or a light source and optical filters corresponding to the fluorescence emission spectra of the staining agent.

8. A composition as claimed in claim 1, wherein the composition comprises a humectant.

9. A composition as claimed in claim 1, wherein the composition comprises from 0.0001% to 1% by weight of Rose Bengal.

10. A kit of parts for use in the detection of biofilms on viable tissue, the kit comprising:
    a composition including a staining agent which preferentially stains biofilms, 0.1 to 2.0% by weight EDTA, 0.1 to 1.0% by weight of a surfactant, and a preservative to provide preservative action in the composition, wherein the staining agent is Rose Bengal, wherein the composition is a non-gelled composition, wherein the composition is in the form of a soluble film, and wherein the preservative includes methyl-paraben, and
    a light source capable of causing the staining agent to fluoresce.

11. A kit as claimed in claim 10, wherein the light source emits light in order to make the staining agent fluoresce.

12. A kit as claimed in claim 10, comprising spectacles or lenses for use in detecting the biofilm wherein the spectacles or lenses act to exclude all wavelengths of light except those at which the staining agent fluoresces.

13. A kit as claimed in claim 10, comprising a wound irrigation solution.

14. A method of detecting a biofilm in a wound comprising:
    obtaining a non-gelled composition including a staining agent which preferentially stains biofilms, 0.1 to 2.0% by weight EDTA, 0.1 to 1.0% by weight of a surfactant, and a preservative in the form of methyl-paraben, wherein the staining agent is Rose Bengal;
    terminally sterilizing the composition using ethylene oxide;
    applying the composition to viable tissue;
    inspecting the tissue for the presence of stained biofilm with the naked eye or with a light source that causes the stained biofilm to fluoresce; and
    detecting the fluorescence emitted from the stained biofilm.

15. The method of claim 14, wherein the composition is a foaming mousse and includes a foaming agent.

16. The method of claim 14, wherein the composition is a soluble film.

17. The method of claim 14, wherein the composition is a lyophilized wafer.

18. The method of claim 14, wherein applying the composition to viable tissue comprises (i) contacting the viable tissue with a soluble film including the composition that has a thickness of at least 0.1 centimeter and (ii) leaving the soluble film in place for at least 2 minutes to permit dissolution of the film.

19. The method of claim 14, wherein applying the composition to viable tissue comprises (i) contacting the viable tissue with a lyophilized wafer including the composition that has a thickness of at least 0.1 centimeter and (ii) leaving the lyophilized wafer in place for at least two minutes to permit dissolution of the wafer.

* * * * *